United States Patent [19]

McPherson et al.

[11] Patent Number: 4,656,159

[45] Date of Patent: Apr. 7, 1987

[54] GALACTOSE-C-6 NITROGEN MUSTARD COMPOUNDS AND THEIR USES

[75] Inventors: Eugene McPherson, Forestville, Md.; Philip S. Schein, Bryn-Mawr, Pa.

[73] Assignee: Georgetown University, Washington, D.C.

[21] Appl. No.: 666,904

[22] Filed: Oct. 31, 1984

[51] Int. Cl.$^4$ .......................... A61K 31/70; C07H 5/06
[52] U.S. Cl. ......................................... 514/25; 514/23; 514/53; 536/4.1; 536/17.1; 536/17.2; 536/18.7; 536/117; 536/118; 536/122
[58] Field of Search ................ 536/22, 4.1, 17.1, 17.2, 536/18.7, 117, 118, 122; 514/42, 23, 25, 53

[56] References Cited

U.S. PATENT DOCUMENTS 2,715,123  8/1955  Hodge ................................... 536/22
3,005,750 10/1961  Flück et al. .......................... 514/42

FOREIGN PATENT DOCUMENTS 747912 12/1966  Canada ................................. 536/22
4200400  1/1942  Japan .................................. 536/22

OTHER PUBLICATIONS

Wampler et al. Can. Res. 35, 1903–1906 (1975).
Reist et al., J. Amer. Chem. Soc., 82, 2025–2029 (1960).
Vargha et al., J. Chem. Soc., 1957, 810–812.

Primary Examiner—Johnnie R. Brown
Attorney, Agent, or Firm—Steinberg & Raskin

[57] ABSTRACT

Compounds of the formula

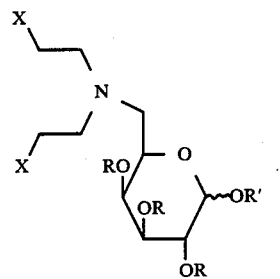

wherein X is halogen; each R independently represents H, a $C_1$–$C_4$ alkyl group, a $C_2$–$C_4$ alkanoyl group, a phosphate group, or a sulfate, sulfonate, or benzoate group with the proviso that no more than one sulfate, sulfonate, or benzoate group is present in said compound; and R' represents R or a carbohydrate residue derived from a carbohydrate having the formula R'OH with the proviso that R' and the R on C-2 or both R groups on C-3 and C-4 together can represent an isopropylidene group; or a pharmaceutically acceptable salt thereof, are disclosed along with methods of synthesizing and using these compounds.

18 Claims, 2 Drawing Figures

Synthetic Scheme for Galactose-C-6 Nitrogen Mustard

GALACTOSE-C-6 NITROGEN MUSTARD COMPOUNDS AND THEIR USES

BACKGROUND OF THE INVENTION

1. Field of the Invention

This invention relates to nitrogen mustard derivatives which possess good antitumor activity against leukemia and other tumors and particularly to nitrogen mustards derived from carbohydrates.

2. Description of the Prior Art

Nitrogen mustards were among the first chemotherapeutic agents rationally applied to the treatment of tumors. In many ways, modern cancer chemotherapy can be said to have begun with the discovery of the clinical activity of certain nitrogen mustards against lymphoid neoplasms during studies made on the biological effects and therapeutic applications of certain chemical warfare agents during World War II. However, the high chemical reactivity of nitrogen mustards and the high probability of nonselective reaction with diverse nucleophilic centers available in vivo result in numerous toxic side effects. In particular, damage to bone marrow and other rapidly dividing normal cells limits the use of basic nitrogen mustards (such as nitrogen mustard itself: 2-chloro-N-(2-chloroethyl)-N-methylethaneamine) limits the usefulness of these compounds. In fact, the damaging effects of nitrogen mustards on bone marrow provided the initial clue which first suggested that the mustards might also affect the growth of lymphoid tumors.

Nitrogen mustard (mechlorethamine) represents the standard for comparison in the mustard class of alkylating agents. It has substantial therapeutic activity for a number of human tumors, including Hodgkin's and non-Hodgkin's lymphomas. It is actively used in the treatment of Hodgkin's disease, as a component of the MOPP regimen (Devita et al, Annals Internal Med. 73, 891-895, 1970). Approximately 70-80% of patients are cured on this regimen. However, the substantial acute and chronic bone marrow toxic properties of nitrogen mustard serve as a severe limiting factor in its clinical use, as discussed above for the class in general. Many patients, at least 20%, require a substantial reduction in dose (perhaps to sub-therapeutic levels) because of extreme depression of white blood cell count. With repeated courses of treatment, there is a threat of cumulative injury with a resultant state of chronic bone marrow hypoplasia. L-PAM (L-phenylalanine mustard) has similar limitations because of severe bone marrow toxicity. In contrast to nitrogen mustard, the nadir of white blood cell count is somewhat delayed with L-PAM, and the injury to the bone marrow is more cumulative.

Numerous derivatives of nitrogen mustard have been synthesized in an effort to reduce toxic effects while retaining the desired chemotherapeutic activity. See, for example, Burger's Medicinal Chemistry 4th Ed., Part II, M. E. Wolff, Ed., John Wiley & Sons, New York, (1979), pages 619-633 for a review of chemotherapeutic alkylating agents, most of which are derivatives of or have structural features in common with nitrogen mustard.

A few amino glucose mustards have been developed in the more recent past and tested for antitumor activity against P388 leukemia and L1210 leukemia (Wampler et al, Can. Res. 35, 1903-1906 (1975)). These compounds employed a glucose moiety carrying a nitrogen mustard at position C-2. Reist et al, J. Amer. Chem. Soc. 82, 2025-2029 (1960) discusses the synthesis of a C-6 glucose mustard without mentioning its possible biological activity. Other sugar mustards showing good activity include 1,6-di-(2-chloroethyl)amino-1,6-dideoxy-D-mannitol dihydrochloride, developed by Vargha et al, J. Chem. Soc., 1957, 810-812.

However, none of these studies have indicated any suppression of damage to bone marrow. Accordingly, there remains a need for therapeutically active compounds which retain their activity against rapidly dividing tumor cells but which have reduced activity against bone marrow.

SUMMARY OF THE INVENTION

Accordingly, it is an object of the present invention to provide a nitrogen mustard derivative which retains high activity against tumor cells but which spares bone marrow.

It is another object of this invention to provide a method for synthesizing such compounds.

These and other objects of the invention as will hereinafter become more readily apparent have been accomplished by providing a compound of the formula

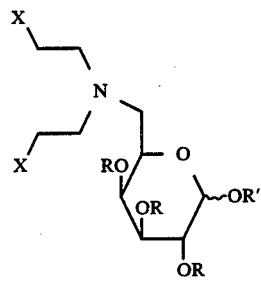

wherein X is halogen; each R independently represents H, a $C_1$-$C_4$ alkyl group, a $C_2$-$C_4$ alkanoyl group, a phosphate group, or a sulfate, sulfonate, or benzoate group with the proviso that no more than one sulfate, sulfonate, or benzoate group is present in said compound; and R' represents R or a carbohydrate residue derived from a carbohydrate having the formula R'OH with the proviso that R' and the R on C-2 or both R groups on C-3 and C-4 together can represent an isopropylidene group; or a pharmaceutically acceptable salt thereof.

BRIEF DESCRIPTION OF THE DRAWINGS

A more complete appreciation of the invention and many of the attendant advantages thereof will be readily obtained by reference to the following detailed description when considered in connection with the accompanying drawings, wherein.

DESCRIPTION OF THE PREFERRED EMBODIMENTS

Figure 1:
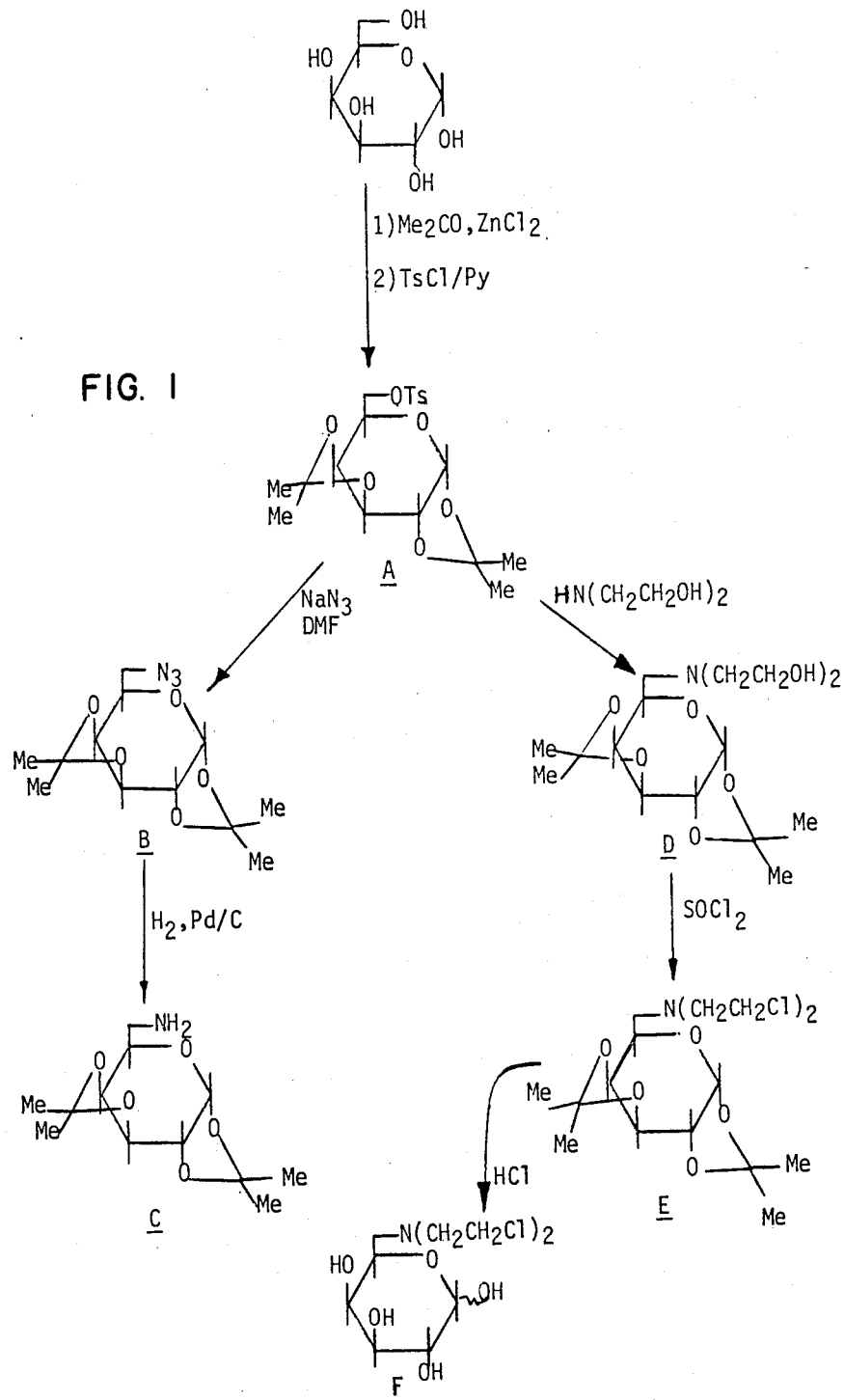
FIG. 1 shows a reaction scheme of the synthesis of galactose-C-6 nitrogen mustard.

The present invention arose in part from the discovery that galactose C-6 nitrogen mustard compounds show full antitumor activity with reduced toxicity to bone marrow. Galactose C-6 nitrogen mustards of the invention are compounds having the formula:

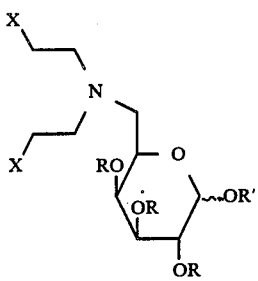

wherein X is halogen; each R independently represents H, a $C_1$–$C_4$ alkyl group, a $C_2$–$C_4$ alkanoyl group, a phosphate group, or a sulfate, sulfonate, or benzoate group with the proviso that no more than one sulfate, sulfonate, or benzoate group is present in said compound; and R' represents R or a carbohydrate residue derived from a carbohydrate having the formula R'OH with the proviso that R' and the R on C-2 or both R groups on C-3 and C-4 together can represent an isopropylidene group; or a pharmaceutically acceptable salt thereof. Although all of these compounds retain the desired chemotherapeutic activity, those which are more hydrophilic and less lipophilic are preferred since such compounds have less tendency to enter tissues or organs high in lipids, such as bone marrow. Accordingly, compounds in which each R on the galactose portion of the molecule is H are preferred. Especially preferred are compounds in which both R and R' all represent hydrogen atoms or in which R' is a carbohydrate residue. When R and R' do not represent H, R and R' should be enzymatically cleavable in the human or animal to which the compound is administered, a result that can readily be detected by standard metabolic studies.

When R or R' is a phosphate, benzoate, sulfate, or sulfonate (i.e., when the compound is a phosphate, benzoate, sulfate, or sulfonate ester), phosphate groups are preferred. Sulfates, sulfonates and benzoates are limited to one such functional group per compound. No such limit is placed on the number of phosphate groups. Preferred sulfonates are $C_1$–$C_4$ alkyl sulfonates, phenylsulfonates, and amino-substituted phenylsulfonates, most preferably p-aminophenylsulfonates.

In the mustard portion of the molecule, X is preferably bromine or chlorine and most preferably chlorine. However, X may also represent fluorine or iodine, and each X may independently represent different halogen atoms, although preferred compounds are those in which both X represent the same halogen.

When R' represents a carbohydrate residue derived from a carbohydrate having the formula R'OH (i.e., the "OH" is one of the hydroxyl groups of the carbohydrate), it is preferred that the carbohydrate be a single 5- or 6- carbon sugar such as glucose, galactose, mannose, ribose, fructose, xylose, or a similar monosaccharide of the formula $C_5H_{10}O_5$ or $C_6H_{12}O_6$. Most preferred are galactose, xylose, mannose, and ribose. As shown in the formula set forth above, the R' moiety is attached to the remainder of the formula through a hemiacetal bond at C-1 of the non-reducing galactose C-6 nitrogen mustard portion of the molecule. As shown in the formula, compounds of the invention can exist as either the α- or β-anomer. Attachment of carbohydrate R'OH is preferably through a C-4 or C-6 (most preferably C-6) hydroxyl for a 6-carbon sugar and through a C-5 hydroxyl for a 5-carbon sugar.

Representative $C_1$–$C_4$ alkyl and alkanoyl groups include methyl, ethyl, t-butyl, acetyl, propionyl and similar groups. Ethyl groups are most preferred. No more than one methyl should be present in order to minimize toxicity.

It is preferred that all R groups on C-2, C-3, and C-4 be the same, although this is not essential.

When a compound of the invention is present as a pharmaceutically acceptable salt, the salt will usually be an acid addition salt formed by reacting an acid with the amino group attached at C-6 of the galactose portion of the molecule. The acid used to form the addition salt can be either a mineral acid or an organic acid. Examples of suitable mineral acids include hydrochloric acid, hydroiodic acid, sulfuric acid, and nitric acid. Suitable organic acids are those having a dissociation constant sufficient to form an acid addition salt. Examples of suitable organic acids include citric acid and lactic acid.

A salt may also be formed at a phosphate or sulfate functional group that is part of the compound. Such salts would typically be alkali metal salts; e.g., —$PO_3$$Na_2$Na or —$PO_3$$K_2$ instead of —$PO_3H_2$ for R or R'.

Taking these preferences into consideration, examples of preferred compounds of the invention include the following:

| Example | R' | R C-2 | C-3 | C-4 | X | salt |
|---|---|---|---|---|---|---|
| 1 | H | H | H | H | Cl | — |
| 2 | galactose | H | H | H | Cl | HCl |
| 3 | —$CH_2CH_3$ | —$CH_2CH_3$ | —$CH_2CH_3$ | —$CH_2CH_3$ | Br | citrate |
| 4 | | $(CH_3)_2C=$ | | $(CH_3)_2C=$ | Cl | — |
| 5 | ribose | —$CH_2CH_3$ | —$CH_2CH_3$ | —$CH_2$—$CH_3$ | Br | lactate |
| 6 | —$PO_3H_2$ | —$PO_3H_2$ | —$PO_3H_2$ | —$PO_3H_2$ | Cl | — |
| 7 | H | $\overset{O}{\underset{\|}{-CCH_3}}$ | $\overset{O}{\underset{\|}{-CCH_3}}$ | $\overset{O}{\underset{\|}{-CCH_3}}$ | Cl | HCl |
| 8 | H | H | $\overset{O}{\underset{\|}{-CCH_3}}$ | $\overset{O}{\underset{\|}{-CCH_3}}$ | Br | — |
| 9 | mannose | —$CH_3$ | H | H | Cl | $HNO_3$ |

-continued

| Example | R' | R C-2 | C-3 | C-4 | X | salt |
|---|---|---|---|---|---|---|
| 10 | xylose | H | H | H | Br | — |
| 11 | galactose | H | H | H | Br | citrate |
| 12 | H | H | H | H | Br | lactate |

The procedures previously known for the preparation of nitrogen mustard derivatives of glucose are not suitable for producing the derivatives of galactose that form the present invention. The crystalline diisobenzylidine derivative of glucofuranose is impractical with a galactose sugar. The yields are extremely low and the isobenzylidene, isopropylidene is extremely difficult to prepare. The 1,2,3,4-diisopropylidene galactose derivative used in the method disclosed herein was selected based on its high yield, the commercial availability of raw starting material, and the low cost of production (Reist et al, J. Amer. Chem. Soc. 82, 2025–2029, 1960). However, all compounds of the invention can be synthesized using the following procedure and modifications thereof readily apparent to those skilled in the art of carbohydrate synthesis.

The first step in the general synthetic procedure is the preparation of a 1,2,3,4-diisopropylidene derivative of galactose. The reaction is generally carried out in dry acetone under an inert atmosphere. Zinc chloride or a similar catalyst is added along with sulfuric acid, after which D-galactose is added. After neutralization of the acid and addition of water, the resulting 1,2,3,4-diisopropylidene derivative is separated from the solvent. This product is then dissolved in a polar aprotic solvent and treated with sodium azide to give the 6-azido derivative. The 6-azido derivative is reduced with a catalyst to give the 6-amino derivative, which was used for structure verification since this is a known compound. The tosylate derivative is treated with diethanolamine in an amino exchange reaction to give the 6-bis-(2-hydroxyethyl)amino derivative. This compound is treated with thionyl chloride to give the 6-bis-(2-chloroethyl)amino derivative. The final product in which R and R' all represent H is obtained from this compound by removal of the isopropylidene protective groups. At this point, R and R' groups can be added using standard techniques of carbohydrate chemistry. General techniques of alkylation, acylation, and formation of disaccharides are well known and are described in many publications such as Vargha et al, J. Chem. Soc., 1957, 805–809; Vargha et al, J. Chem. Soc., 1957, 810–812; Horton, J. Org. Chem., 29, 1776–1782 (1964); and Suami et al, J. Med. Chem., 22, 247–250 (1979); which are all incorporated herein by reference.

Compounds of the invention can be used to selectively suppress cell division in hydrophilic tissue while minimizing undesired side reactions in lypophilic tissue by administering an amount of one or more compounds of the invention sufficient to suppress cell division to a mammal. Freireich et al, Cancer Chemo. Rept. 50, 219–244 (1966), compared the quantitative toxicity of 18 anticancer drugs in six species after correcting the data to a uniform schedule of treatment for five consecutive days. This analysis demonstrated that mouse, rat, dog, human, monkey, and man have essentially the same maximum tolerated dose (MTD) when compared on a basis of mg/m$^2$ of body surface area. The study suggested that Phase I clinical trials could be safely initiated at a dose one-third the animal MTD. The mouse was as useful as any other species in this regard on which to base the calculation. The appropriate therapeutically effective dose for any compound of the invention can therefore be determined readily by those skilled in the art from simple experimentation with laboratory animals, preferably mice, and will usually be within the range from about 4 to about 8 mg/kg of body weight, preferably from about 5 to about 6 mg/kg. Tumors, the growth of which may be suppressed, include those listed in Holland and Frei, Cancer Medicine, Lea and Febiger, Philadelphia, 1973, which is herein incorporated by reference. Tumors which are preferred to be treated include those already known to be sensitive to nitrogen mustard and L-PAM, such as Hodgkin's and non-Hodgkin's lymphomas.

Although treatment of any mammal, (e.g., cattle, horses, dogs, and cats) is encompassed by this invention, treatment of humans is especially preferred.

The mode of administration of compounds of the invention may be by any suitable route which delivers the compound to the system being treated. For the purposes of the present invention, the compounds may be administered orally, topically, parenterally, intraperitoneally, or by any other method which enables the active ingredient to reach the site being treated. The term parenteral as used herein includes subcutaneous, intravenous, intramuscular, intrasternal, and infusion techniques. Intravenous injection is the preferred method of administration.

Compounds of the invention may be prepared into pharmaceutical compositions containing the active ingredient in a form suitable for any of the usages previously described. For example, a pharmaceutical composition suitable for oral use may be in the form of, for example, a tablet, troche, lozenge, aqueous or oral suspension, dispersible powder or granule, emulsion, hard or soft capsule, syrup, or elixir. Compositions intended for oral use may be prepared according to any method known in the art for the manufacture of pharmaceutical compositions and may contain one or more agents selected from the group consisting of sweetening, flavoring, coloring, and preserving agents. Tablets containing the active ingredient in admixture with non-toxic pharmaceutically acceptable excipients may be prepared by any method suitable for the manufacture of tablets. Excipients may include, for example, inert diluents, such as calcium carbonate or lactose; granulating and disintegrating agents, such as maize starch or algenic acid; binding agents, such as starch and gelatin; and lubricating agents, such as magnesium stearate and talc. The tablets may be uncoated or they may be coated by any known technique to delay disintegration and absorption in the gastrointestinal tract and thereby provide a sustained action over a long period.

Aqueous suspensions containing the active material in admixture with excipients suitable for the manufacture of aqueous suspensions may also be prepared. Such excipients include suspending agents, such as methyl cellulose, dispersing or wetting agents such as lecithin and condensation products of an alkylene oxide with a fatty acid, such as polyoxyethylene stearate; or similar materials. The aqueous suspension may also contain a preservative, such as p-hydroxybenzoate, a coloring agent, a flavoring agent, or a sweetening agent.

Oily suspensions may be formulated by suspending the active ingredient in a vegetable oil or mineral oil. The oil suspensions may contain a thickening agent, such as beeswax. Sweetening agents, flavoring agents, and preserving agents, such as those described above, may also be used.

Other pharmaceutical preparations may be prepared by any of the techniques now known to the pharmaceutical arts.

It is preferred that the compounds of the invention, when in the form of pharmaceutical preparations, are present in unit dosage forms. When intended for human use, these amounts can easily be calculated from the dosage rates previously given by assuming a body weight of 70 kg. Accordingly, a preferred unit-dose-containing pharmaceutical preparation would contain from about 300 to about 375 mg of active ingredient. It will be understood, however, that the specific dose level for any particular patient will depend upon a variety of factors including the activity of the specific compound employed; the age, general health, sex, and diet of the patient; the time of administration; the route of administration; the rate of excretion; possible synergistic effects with any other drugs being administered; and the severity of the particular disease being treated.

The invention now being generally described, the same will be better understood by reference to certain specific examples which are included herein for purposes of illustration only and are not intended to be limiting of the invention or any embodiment thereof, unless specified.

Example 1: Synthesis of 6-Bis-(2-Chloroethyl)Amino-6-Deoxy-D-Galactopyranose Hydrochloride (F)

A synthesis scheme for the production of galactose-C-6-nitrogen mustard is shown in FIG. 1.

I. Preparation of Compound A; 1,2,3,4-Diisopropylidene-6-0-p-Tolylsufonyl-α-D-Galactopyranose Anhydrous zinc chloride (43.2 g) was rapidly added to a flask containing 450 ml of dry acetone under a dry nitrogen atmosphere with vigorous stirring. Concentrated sulfuric acid (1.74 ml) was added dropwise; then 36 g of D-galactose (anhydrous) was added and stirring continued for 4½ hours. A suspension of anhydrous sodium carbonate (72 g) in 126 ml of water was added in small portions. The suspension was filtered and washed with several portions of acetone. The filtrate and washings were combined and evaporated in vacuo to remove the acetone. The upper oily layer was then extracted with ether, and the ether was dried over anhydrous sodium sulfate. Then ether was removed in vacuo to give a syrup-like liquid (46 g) of the 1,2,3,4-diisopropylidene-α-D-galactopyranose which was purified by distillation (vacuum).

This distilled product (30 g) and 33 g of p-toluenesulfonylchloride were added to 60 ml pyridine (dried over molecular sieves) in a flask protected from moisture and kept at room temperature overnight. Water was added to dissolve the pyridine.HCl, and additional water was added with stirring until crystallization was complete. The crystals were washed with water and recrystallized from hot ethanol after treatment with charcoal to give compound A, m.p. 101°-102° C., NMR (Acetone-d$_6$), tosyl group 7.4–7.8δ; α-D anomeric protons 5.3δ, J$_{1,2}$=4.8 cps.

II. Preparation of 1,2,3,4-Diisopropylidene-6-azido-6-deoxy-α-D-galactopyranose; Compound B Compound A (18.6 g) was dissolved in 150 ml of dimethylformamide (dried over molecular sieves) in a flask protected from moisture. Sodium azide (7.8 g) was added with stirring, and the mixture was heated at 120 C for 36 hours. The mixture was then evaporated to dryness in vacuo, and the residue was suspended in water and methylene chloride; The aqueous layer was then separated. The methylene chloride layer was washed several times with water and dried over anhydrous sodium sulfate. Then the methylene chloride was removed in vacuo to give a syrupy liquid. NMR (CDCl$_3$): no tosyl group in region 7.4–7.8δ; IR (ETOAC): N$_3$, 2090 cm strong band. This is compound B.

Compound B (4 g) was dissolved in ethyl acetate (200 ml) along with 0.4 g of 5% Pd/C and hydrogenated at 1 atmosphere and room temperature for 5 hours to give the amine derivative, compound C. IR$_1$ (ETOAC): broad band at 2800–3400 cm$^{-1}$ and disappearance of band at 2090 cm$^{-1}$. This is compound C.

III. Preparation of 1,2,3,4-Diisopropylidene-6-Bis-(2-Hydroxyethyl)amino-6-Deoxy-α-D-Galactopyranose; Compound D Twenty-one grams of compound A were suspended into 225 ml of freshly distilled diethanolamine and heated at 150°-160° C. for 4–4½ hours under a dry nitrogen atmosphere with vigorous stirring. The amber colored viscous mixture was cooled to room temperature and added to 800 ml of methylene chloride. The methylene chloride solution was washed with 250 ml portions of water 2× and back extracted with fresh methylene chloride (100 ml). The methylene chloride extracts were combined and dried over anhydrous sodium sulfate. Concentration in vacuo gave 16 g of an amber syrup. NMR (CDCl$_3$): disappearance of tosyl group at 7.4–7.8δ.

IV. Preparation of 1,2,3,4-Diisopropylidene-6-Bis-(2-Chloroethyl)amino-6-Deoxy-α-D-Galactopyranose; Compound E Compound D (2 g) was dissolved in 25 ml of dry methylene chloride and 6 ml of thionyl chloride, refluxed for 15 minutes, and immediately evaporated to dryness in vacuo followed by repeated co-evaporation with fresh dry methylene chloride. A sample of this product was set aside for NMR analysis which was consistent with the proton splitting pattern for haloethyl compounds (a triplet of triplets, 2.5–3.9δ). Isopropylidene methyl groups were also indicated by peaks at 1.3–1.5δ.

V. Preparation of 6-Bis-(2-Chloroethyl)amino-6-Deoxy-D-Galactopyranose Hydrochloride; Compound F Without further purification compound E (1. Og) was added to 10 ml of 6N HCl in a small flask fitted with a reflux condenser and refluxed for 10 minutes. The solution was then cooled to room temperature, extracted 2× with methylene chloride, and treated with charcoal.

The aqueous solution was lyophilized to give 450 mg of pale white crystals, which were hydroscopic. NMR (D$_2$O): 3.4–4.6δ, galactose and N-(CH$_2$CH$_2$Cl)$_2$ protons; HDO, 4.8δ; 5.3 and 5.6δ, alpha and beta anomeric protons respectively; disappearance of isopropylidene protons (methyl groups) at 1.3–1.5δ. Anal.: Calcd. for C$_{10}$H$_{20}$O$_5$NCl$_3$. 4H$_2$O: C, 29.05; H, 6.78; N, 3.38; Found: C, 28.43; H, 6.03; N, 3.28.

Example 2: Animal Studies

Normal CD2F$_1$ male mice, 6–9 weeks old, were used for initial studies to determine toxic single doses of compound F in mice. Doses of the compound in the range of the LD$_{10}$ dose (single intraperitoneal dose that produces toxic deaths in 10% of the normal mice) were then tested for antitumor activity against several murine tumor systems. The LD$_{10}$ dose was then evaluated in normal CD2F$_1$ mice for effects on the hemapoietic system.

Determination of Toxic Doses of the Compound in Normal Mice

Normal CD2F$_1$ male mice were used to determine the LD$_{10}$ dose (single intraperitoneal dose toxic to 10% of normal mice) for the compound. Various concentrations of the compound were prepared immediately prior to use by dissolving the drug in physiological saline (on ice) and administering intraperitoneally (i.p.) in a volume of 0.1 ml/10 grams body weight. The normal mice were then observed for up to 45 days post drug administration to determine deaths due to acute and chronic (up to 45 days) drug toxicity. Results are summarized in the following table:

| Dose (mg/kg) | Dose (μmol/kg) | Deaths due to drug toxicity |
|---|---|---|
| 14 | 33.3 | 0/10 (LD$_0$) |
| 15.5 | 37 | 1/10 (LD$_{10}$) |
| 18 | 43 | 2/10 |
| 22.5 | 53.4 | 7/10 |
| 27 | 64 | 10/10 (LD$_{100}$) |

The approximate LD$_{10}$ dose of the compound (single i.p. dose toxic to 10% of normal mice) was 15.5 mg/kg or 37 μmol/kg; single doses in this range were used to evaluate antitumor activity in two murine tumor systems.

Determination of Murine Antitumor Activity

The murine P388 leukemia system, maintained intraperitoneally in female DBA/2 mice, was used to evaluate antitumor activity. This tumor was selected because of its known sensitivity to nitrogen mustard (HN2) and L-phenylalanine mustard (L-PAM). The water-soluble drugs (the galactose mustard compound and nitrogen mustard) were dissolved in saline (on ice) immediately prior to use and administered i.p. in a volume of 0.1 ml/10 grams body weight. L-PAM was dissolved in one milliliter of ethanol containing 40 μl of concentrated HCl, and this was added to a 0.3% solution of hydroxypropyl cellulose (HPC) in saline to give a final concentration of 4% ethanol and 96% HPC - containing saline.

Each drug was administered to groups of 10 CD2F$_1$ male mice on day one after implantation of 1×10$^6$ P388 leukemia cells i.p. (in a volume of 0.10 ml). The P388 antileukemic activity of the test galactose mustard compound was assessed by mean survival days, percentage increased life span (%ILS), and number of survivors after 45 days. The percentage ILS was calculated as follows % ILS = $(T - C)/C \times 100$ where $T$ is the mean survival days of the treated mice and $C$ is the mean survival days of the untreated mice.

P388 antileukemic activity of the test galactose mustard compound was compared to that achieved with two clinically used nitrogen mustard compounds: nitrogen mustard (HN2) and L-phenylalanine mustard (L-PAM). The results are summarized in the following table:

| Drug | Dose (mg/kg) | Dose (μmol/kg) | Mean survival (days) | % ILS |
|---|---|---|---|---|
| gal. mustard compound | 15.5* | 37 | 19.5 | 107 |
|  | 18δ | 43 | 15.9 | 69 |
| nitrogen mustard (HN2) | 2.9* | 15.1 | 15.0 | 60 |
|  | 3.5δ | 18.2 | 12.3 | 31 |
| L-phenyl alanine mustard (L-PAM) | 12* | 39 | >21.5 | >129 |
|  | 15δ | 48.8 | >19.1 | >103 |

*approximate LD$_{10}$ dose
δapproximate LD$_{20}$ or LD$_{25}$ dose

When antitumor activities against the murine P388 leukemia (a single LD$_{10}$ dose administered i.p. on day one after implantation of 10$^6$ P388 cells intraperitoneally) are compared, overall survivals for the galactose mustard compound were significantly greater (p<0.05) than survivals for nitrogen mustard. Four out of 30 mice receiving the LD$_{10}$ dose of L-PAM (12 mg/kg) were long term survivors, living more than 45 days; there were no long term survivors for either nitrogen mustard or the galactose mustard compound.

The Ehrlich ascites tumor system was used as an additional murine tumor system for confirmation of therapeutic activity. Ehrlich ascites was maintained intraperitoneally in female BALB/C mice. Treatment as described in the previous section was administered on day one after implantation of 2×10$^6$ cells/0.10 ml in male BD2F$_1$ mice (6–9 weeks old). The mean survival of untreated tumored mice was 15 days. On days 29 and 40, the number of mice surviving was:

| | | Number of surviving mice | |
|---|---|---|---|
| Drug | Dose (mg/kg) | day 29 | day 40 |
| gal. mustard | 15.5 | 8/10 | 6/10 |
| nitrogen mustard (HN2) | 2.9 | 7/10 | 7/10 |
| L-PAM | 12 | 8/10 | 6/10 |

These initial studies with the Ehrlich ascites suggest that the galactose mustard compound has antitumor activity comparable to nitrogen mustard and L-PAM in this system.

Determination of the Effects of the Compound on the Hematopoietic System in Mice Effects on peripheral leukocyte (WBC) count.

Measurement of peripheral leukocyte (WBC) count was performed using a 20-μl sample of retro-orbital sinus blood obtained from normal CD2F$_1$ male mice on days 3, 4, 5 or 10 following i.p. administration of doses in the range of the $LD_{10}$; groups of 10 mice were treated with drug as described previously. Blood samples obtained were diluted in 9.98 ml of Isoton (a neutral, isotonic buffer solution) and counted in a Coulter counter after lysis with Zapoglobin (an enzyme solution which lyses red blood cells but not white blood cells). WBC differential counts were performed on Wright-stained smears. WBC and absolute neutrophil counts are expressed as a percentage of values from control mice receiving drug vehicle only.

Figure 2:
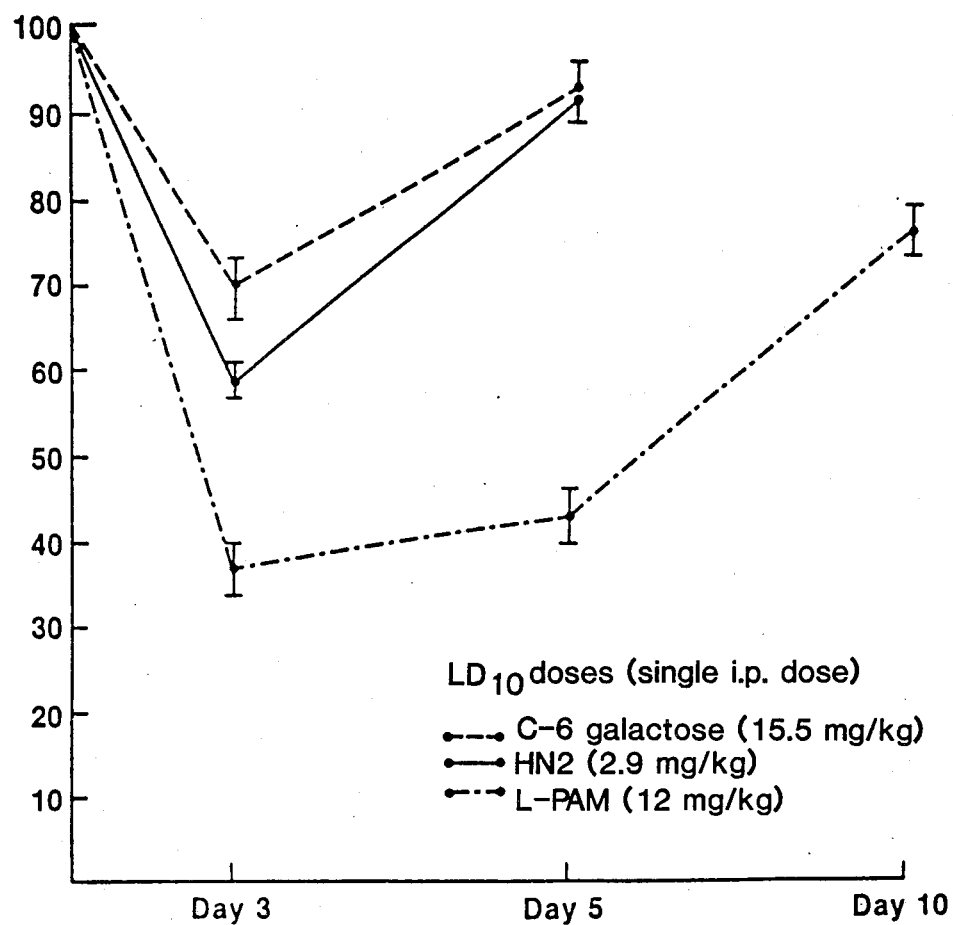
FIG. 2 shows a plot of in vivo effects on peripheral leukocyte (WBC) count after administration of nitrogen mustard (HN2; a control reference compound), L-phenylalanine mustard (L-PAM; a control compound), or the C-6-galactose mustard compound, an indication of the effect of these compounds on bone marrow cells which produce the peripheral leukocytes.

FIG. 2 presents the results of the peripheral leukocyte (WBC) depression study. The nadir for the galactose mustard compound occurred on day 3 after drug administration and was 74% of control. For nitrogen mustard, the nadir WBC also occurred on day 3 and was 57% of control. For the galactose compound, the WBC count recovered to control values by day 4, while animals receiving nitrogen mustard did not recover to control values until day 5. L-PAM produced a more prolonged WBC nadir, with WBC counts reduced to approximately 40-45% of control from days 3 through 5. By day 10 after drug administration, the WBC counts for the L-PAM treated mice had only recovered to 77% of control. Absolute neutrophil counts for the galactose compound were not significantly different from control (94% of control). In contrast, nitrogen mustard produced a nadir absolute neutrophil count of 70% of control on day 3, and L-PAM produced a nadir absolute neutrophil count of 50% of control on day 4. In summary, the galactose compound produced minimal WBC depression and no significant decrease in absolute neutrophil count at the $LD_{10}$ dose that produced antitumor activity against the murine P388 leukemia superior to that achieved with a comparable $LD_{10}$ dose of nitrogen mustard.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A compound of the formula

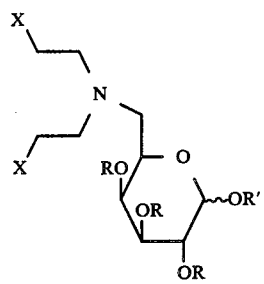

wherein X is halogen; each R independently represents H, a $C_1$-$C_4$ alkyl group, a $C_2$-$C_4$ alkanoyl group, a phosphate group, or a sulfate, sulfonate, or benzoate group with the proviso that no more than one sulfate, sulfonate, or benzoate group is present in said compound; and R' represents R or a carbohydrate residue derived from a carbohydrate having the formula R'OH with the proviso that R' and the R on C-2 or both R groups on C-3 and C-4 together can represent an isopropylidene group, or a pharmaceutically acceptable salt thereof.

2. The compound of claim 1 wherein R' is H or a carbohydrate residue of galactose, xylose, mannose, or ribose.

3. The compound of claim 2 wherein each R is H.

4. The compound of claim 3 wherein said compound is an acid addition salt.

5. The compound of claim 3 wherein X is Br.

6. The compound of claim 3 wherein X is Cl.

7. The compound of claim 1 wherein said compound is an acid addition salt.

8. The compound of claim 7 wherein said acid is HCl, $H_2SO_4$, citric acid, or lactic acid.

9. The compound of claim 7 wherein said acid is HCl.

10. The compound of claim 7 wherein each R is H.

11. The compound of claim 8 wherein R' and each R is H.

12. The compound of claim 11 wherein X is Cl.

13. The compound of claim 12 wherein said acid is HCl.

14. A method of selectively suppressing cell division in hydrophylic tissue over lyophylic tissue, which comprises: administering to a mammal an amount of a compound of claim 1 sufficient to suppress cell division in a hydrophylic tissue.

15. The method of claim 14 wherein said amount is from 4 to 8 mg/kg.

16. The method of claim 14 wherein each R is H.

17. The method of claim 16 wherein R' is H or a carbohydrate residue of galactose, xylose, mannose, or ribose.

18. The method of claim 17 wherein said administering is by intravenous injection.

* * * * *